(12) United States Patent
Scherer et al.

(10) Patent No.: US 11,942,215 B2
(45) Date of Patent: Mar. 26, 2024

(54) SYSTEMS AND METHODS FOR IDENTIFYING AND CORRECTING DEFECTS IN HEALTH CARE SERVICES

(71) Applicant: Motive Medical Intelligence, San Francisco, CA (US)

(72) Inventors: Julie A. Scherer, Emerald Hills, CA (US); Richard S. Klasco, Englewood, CO (US); Nicolapagos A. Rains, Austin, TX (US); Larie H. Smoyer, Stevensville, MT (US); Charles M. Wikman, Minneapolis, MN (US); Jeanne Cohen, San Francisco, CA (US)

(73) Assignee: Motive Medical Intelligence, San Francisco, CA (US)

( * ) Notice: Subject to any disclaimer, the term of this patent is extended or adjusted under 35 U.S.C. 154(b) by 0 days.

(21) Appl. No.: 17/867,514

(22) Filed: Jul. 18, 2022

(65) Prior Publication Data

US 2024/0021295 A1 Jan. 18, 2024

(51) Int. Cl.
*G16H 40/20* (2018.01)
(52) U.S. Cl.
CPC .................................. *G16H 40/20* (2018.01)
(58) Field of Classification Search
CPC ........ G16H 40/20; G16H 10/00; G16H 15/00; G16H 10/60; G16H 50/70; G16H 70/20
See application file for complete search history.

(56) References Cited

U.S. PATENT DOCUMENTS

| 2014/0100863 | A1* | 4/2014 | Mantz | G06Q 10/10 |
| | | | | 705/2 |
| 2014/0201126 | A1* | 7/2014 | Zadeh | A61B 5/7267 |
| | | | | 706/52 |
| 2020/0075164 | A1* | 3/2020 | Lieberman | G06N 20/00 |
| 2021/0204884 | A1* | 7/2021 | Ravishankar | A61B 5/316 |
| 2021/0265051 | A1* | 8/2021 | Bayyana | G16H 50/20 |

OTHER PUBLICATIONS

Siqin et al. ("Can Physicians Identify Inappropriate Nuclear Stress Tests?", Circulation: Cardiovascular Quality and Outcomes vol. 8, Issue 1, Jan. 2015; pp. 23-29).*

(Continued)

*Primary Examiner* — Mark Holcomb
(74) *Attorney, Agent, or Firm* — Carr & Ferrell LLP

(57) ABSTRACT

The disclosure pertains to a secure intelligent networked system for identifying and correcting a defect in a health care service and method for using the same. The system receives data regarding patient care, generally obtained from commercial insurance claims, customer claims or Medicare claims. The system operates on a plurality of nodes configured based on a set of metrics associated with the appropriateness of health care measures. The system may generate a determination regarding the appropriateness of the measure. The system may further produce a second determination denoting a physician's overall conformity with appropriate standards of practice. Finally, the system may generate a knowledge narrative indicating an appropriate action.

21 Claims, 10 Drawing Sheets

(56) References Cited

OTHER PUBLICATIONS

Ladapo JA, Blecker S, Douglas PS. Physician decision making and trends in the use of cardiac stress testing in the United States: an analysis of repeated cross-sectional data. Ann Intern Med. Oct. 7, 2014;161(7):482-90. doi: 10.7326/M14-0296. PMID: 25285541; PMCID: PMC4335355. (Year: 2014).*

Gupta MD, Kunal S, Girish MP, Gupta A, Yadav R. Artificial intelligence in cardiology: The past, present and future. Indian Heart J. Jul.-Aug. 2022;74(4):265-269. doi: 10.1016/j.ihj.2022.07.004. Epub Jul. 30, 2022. PMID: 35917970; PMCID: PMC9453051 (Year: 2022).*

Boxwala et al., "A multi-layered Framework for Disseminating Knowledge for Computer-based Decision Support," Journal of the American Medical Informatics Association, vol. 18, Issue Supplement_1, https://doi.org/10.1136/amiajnl-2011-000334, Nov. 3, 2011, pp. 1132-1139.

National Academy of Medicine, "Optimizing Strategies for Clinical Decision Support," Summary of a Meeting Series, The Learning Health System Series, Tcheng et al. (eds), 2017, 96 pages.

IBM Cloud Learn Hub, "What are Neural Networks," IBN Cloud Education, Aug. 17, 2020, available online <URL: https://www.ibm.com/cloud/learn/neural-networks>, 13 pages.

* cited by examiner

1

SYSTEMS AND METHODS FOR IDENTIFYING AND CORRECTING DEFECTS IN HEALTH CARE SERVICES

FIELD OF THE TECHNOLOGY

Embodiments of the present disclosure relate to the technical field of data analysis, and more specifically, but not by limitation, to applications in health care services.

SUMMARY

This summary is provided to introduce a selection of concepts in a simplified form that are further described in the detailed description below. This summary is not intended to identify key features or essential features of the claimed subject matter, nor is it intended to be used as an aid in determining the scope of the claimed subject matter.

Exemplary embodiments provide systems and methods for identifying and correcting defects in the cost, quality, and appropriateness of health care services.

Exemplary systems include: a secure intelligent networked system for processing data for a physician-directed health care service, such as a treatment plan. The data may be in the form of unstructured narrative text. The system comprises a plurality of input and output nodes, as well as intermediary nodes configured based on a set of metrics associated with the appropriateness of care. The metrics may include information regarding the cost of health care services like those directed by the physician, or regarding the standard of care in the physician's specialty or region of practice, or other information related to the appropriateness of a health care service.

Subsequently, according to exemplary embodiments, the input data are operationalized to produce a ranking of the appropriateness of the physician-directed health care service. A plurality of such rankings may be fed back into the system to determine overall appropriateness of health care services.

Exemplary methods include the method of using the secure intelligent networked system for processing data for a physician-directed health care service. The method includes submitting such data with any level of operable structure, including unstructured narrative text. The method further comprises the use of a plurality of input and output nodes, as well as intermediary nodes configured based on a set of metrics associated with the appropriateness of care. The metrics may include information regarding the cost of health care services like those directed by the physician, or regarding the standard of care in the physician's specialty or region of practice, or other information related to the appropriateness of a health care service.

Subsequently, according to exemplary methods, the input data are operationalized to produce a ranking of the appropriateness of the physician-directed health care service. This ranking may be compared to similar rankings to determine whether the service is appropriate considering expert opinion or the relevant standard of care. A plurality of such rankings may be used as a benchmark for appropriateness of health care services. Individually, the ranking may be used to alter or validate the decision to implement the physician-directed healthcare service.

According to some exemplary embodiments, the system produces an output which in turn produces an outcome, which in turn produces an input. In some embodiments, the output may become the input.

BRIEF DESCRIPTION OF THE DRAWINGS

Exemplary embodiments are illustrated by way of example and not limitation in the figures of the accompanying drawings, in which like references indicate similar elements.

DETAILED DESCRIPTION

Figure 1:
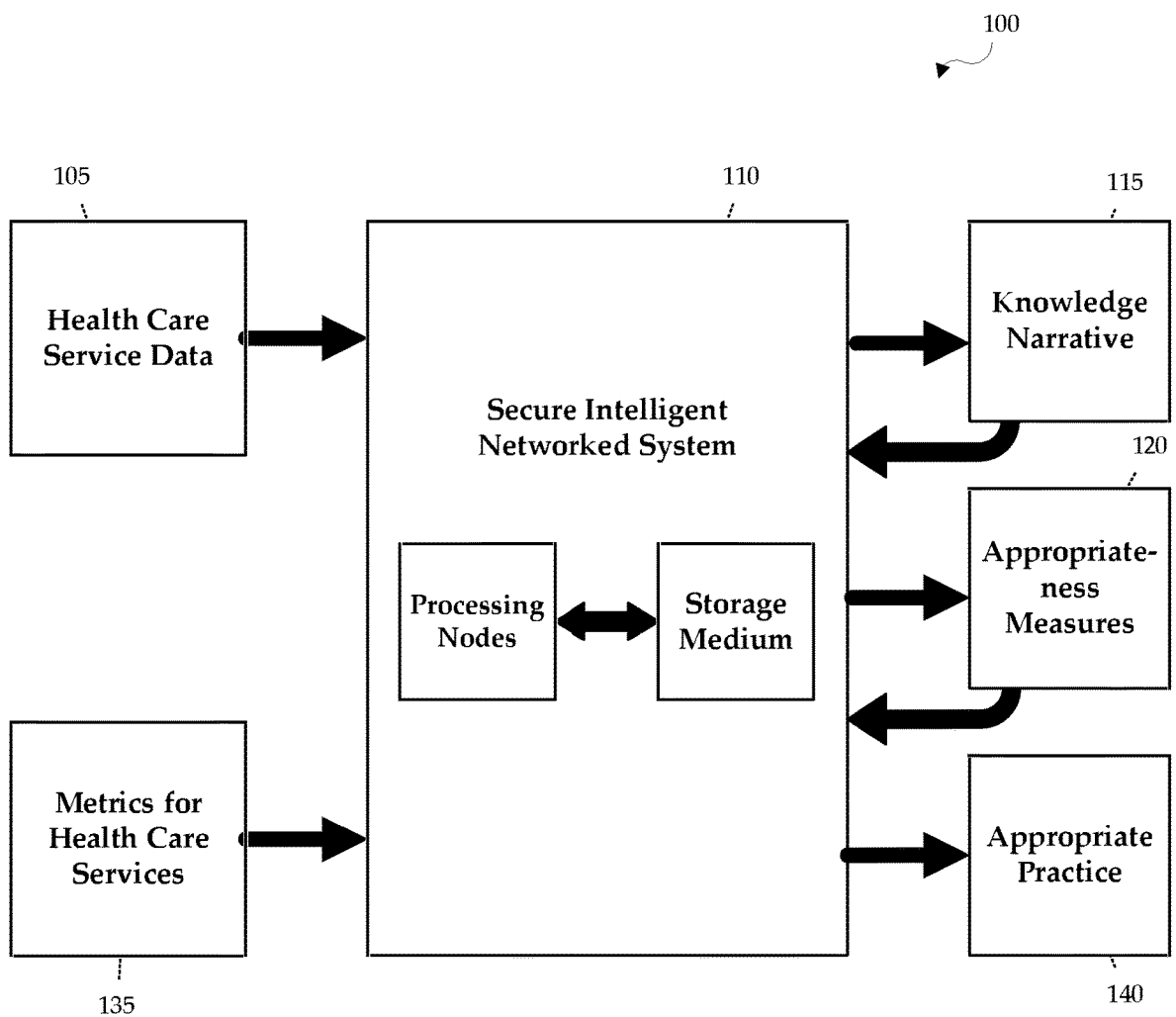
FIG. 1 is a flowchart of an example method of the present disclosure.

The elements identified throughout are exemplary and may include various alternatives, equivalents, or derivations thereof. Various combinations of hardware, software, and computer-executable instructions may be utilized. Program modules and engines may include routines, programs, objects, components, and data structures that effectuate the performance of a particular task when executed by a processor. Computer-executable instructions and associated data structures stored in a computer-readable storage medium represent examples of programming means for executing the steps of the methods and/or implementing particular system configurations disclosed herein.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present disclosure. As such, some of the components may have been distorted from their actual scale for pictorial clarity.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments.

Depending on the context of discussion herein, a singular term may include its plural forms and a plural term may include its singular form. Similarly, a hyphenated term may be occasionally interchangeably used with its non-hyphenated version, a capitalized entry may be interchangeably used with its non-capitalized version, and an italicized term may be interchangeably used with its non-italicized version. Such occasional interchangeable uses shall not be considered inconsistent with each other.

Identification of Defects

The present disclosure describes systems and methods for the rapid identification of defects in health care services, and further, the correction of defects.

The term "defect" refers to decisions or behaviors that result in low-value or inappropriate care, or waste in health care delivery systems. A health care system that minimizes defects can more effectively maximize safety and quality, as well as minimize cost and waste.

A common type of defect is inappropriate care, which deviates from evidence-based practices and can expend limited resources.

Appropriateness measures are measures designed to reduce the occurrence of defects in health care services. Appropriateness measures include measures that discourage deviation from evidence-based practices or that reduce waste.

Appropriateness measures may reduce the incidence of overuse or underuse of a health care action. By way of example, appropriateness measures would include reducing the incidence of mammography screening underuse in eligible women, physical therapy underuse before lumbar surgery, or nuclear imaging overuse in stress testing.

Appropriateness measures can be tools for making visible and correcting defects. Appropriateness measures are built on a conjoint analysis of cost, quality, and potential for harm. This foundation aligns the interests of payers, providers, and patients.

Efforts that individually optimize cost, quality, and safety frequently fail to acknowledge the implicit tradeoffs that appropriateness demands. Costs must be constrained but not at the expense of quality; quality is desirable but not at all costs; and safety concerns cannot be allowed to thwart potentially lifesaving treatments that entail risk.

Intelligent Clinical Decision Support

Clinical Decision Support provides patients, health care providers, payors, and other individuals with knowledge and person-specific information that is intelligently filtered and presented when needed or requested. Clinical Decision Support can significantly improve quality, safety, efficiency, and effectiveness of health care services.

Clinical Decision Support requires computable biomedical knowledge, person-specific data, and a reasoning or inferencing mechanism that will generate useful information based on the knowledge and data. An important goal is to receive such information as care is being delivered.

Traditionally, practice guidelines and quality officers were relied upon to determine the appropriateness of a health care action. However, reliance on practice guidelines and quality officers can be inefficient due to time delays. Such reliance is also frequently not scalable or extensible and is often seen as subjective rather than quantifiable.

The systems and methods disclosed herein allow appropriateness measures to be constructed as machine-executable knowledge objects, allowing them to be run effectively against big data. In this way, appropriateness measures may be quantifiable, scalable, extensible, and more readily accessible by end users.

In the systems and methods disclosed herein, the appropriateness of a health care action may be determined based on evidentiary support such as medical journals, health studies, clinical guidelines, standards bodies, or subject matter expert panels.

Moreover, the input received from such evidentiary support may be quantified, operationalized, and processed by way of an evidence engine implemented on a secure intelligent communications network. The secure intelligent communications network may be implemented on a system comprising a processor to execute instructions stored in memory and performing asynchronous processing with a computing device. Some or all of the activities occur over one or more network/communication links and may occur in a cloud computing system or edge computing system.

The secure intelligent communications network may further be implemented on a deep-learning environment such as a deep neural network consisting of an input node, a plurality of intermediary nodes, and an output node, each node having weights, biases, functions, and thresholds that are implemented and tuned for optimally useful results.

In these embodiments, each node connects to another node and has an associated weight and threshold. If the output of any individual node is above a specified threshold value, that node will transmit data to the next node within the network. If the output of any individual node is below a specified threshold value, no data will be transmitted to the next node.

Neural networks in such embodiments rely on training data to develop and improve accuracy over time. Once finely tuned for precision, the networks are powerful tools that allow for classification, clustering, and processing large amounts of data at high speeds.

Further, in these embodiments, once an input layer is established, weights are assigned. Such weights help determine the importance of a variable, with larger weights contributing in greater proportion to the output compared to smaller weights. The inputs are multiplied by their respective weights and added together, after which an activation function is applied to the result. If the output exceeds a given threshold, the node is activated, and will transmit data to the next node in the network.

While some embodiments are feedforward, with data flowing only in the direction of input to output, it should be noted that further embodiments may be trained through backpropagation. In such embodiments, data may be transmitted from the output node toward the input node, allowing for calculation and attribution of error associated with each node. Parameters may be adjusted accordingly.

Further, according to some exemplary embodiments, the system produces an output which in turn produces an outcome, which in turn produces an input. In some embodiments, the output may become the input.

FIG. 1 shows an exemplary implementation 100 of the disclosed systems and methods. Within the secure intelligent networked system 110, clinical input may be assigned operative values with various levels of structure, from Boolean operators to coded information interpretable by Clinical Decision Support systems.

The clinical input may include patient health care data received from commercial insurance claims, customer claims, or Medicare claims, or other physician-submitted data sources 105.

The secure intelligent networked system may be configured to perform a series of operations on the received clinical input. Such configuration may include additional inputs from subject matter panels or clinical data 135, or may include weighted values across a plurality of nodes, the weights being associated with values pertaining to cost, quality, and appropriateness of care.

The secure intelligent networked system may generate a number of useful outputs from these operations, including, for example, a knowledge narrative 115. Such knowledge narrative may include a plain text recommended health care action.

By way of example, a knowledge narrative may indicate "75 milligrams of acetaminophen."

The knowledge narrative may be distilled with further iterations to account for nonviable knowledge narratives.

By way of example, a knowledge narrative such as "75 milligrams of acetaminophen" may not be viable for some allergies or comorbidities. In such cases, the set of metrics may be adjusted to account for such nonviability.

The secure intelligent networked system may further produce an additional output denoting a physician's Appropriateness Measures Score 120.

The Appropriateness Measures score refers broadly to the of ranking a physician's use of appropriate and inappropriate actions regarding a specific type of health care service.

In one embodiment, the method first takes the percentage of cases handled by the physician with inappropriate care actions out of cases handled by the physician that qualify for the care action.

As appropriate, cases may be excluded from the overall number of qualifying cases if complicating factors, increased risk, or urgent or emergent circumstances are present.

By way of example, an Appropriateness Measures Score may be determined for cardiovascular stress testing by evaluating a physician's number of inappropriate stress tests out of the number of all stress test cases.

Such inappropriate stress tests may include, by way of example, overuse of nuclear stress testing, which in some circumstances may impose significant patient cost burden, and can be avoided by ordering alternative diagnostic testing.

Numerator cases in this example would include stress testing with nuclear imaging that occurred within 30 days of an evaluation and management visit to a cardiologist. Denominator cases would include stress testing that occurred within 30 days of a cardiologist evaluation and management visit. Excluded cases would include inpatients, outpatients with symptoms of Acute Coronary Syndrome, or patients who had a cardiac-related emergency department visit during the 30-day period.

Figure 2:
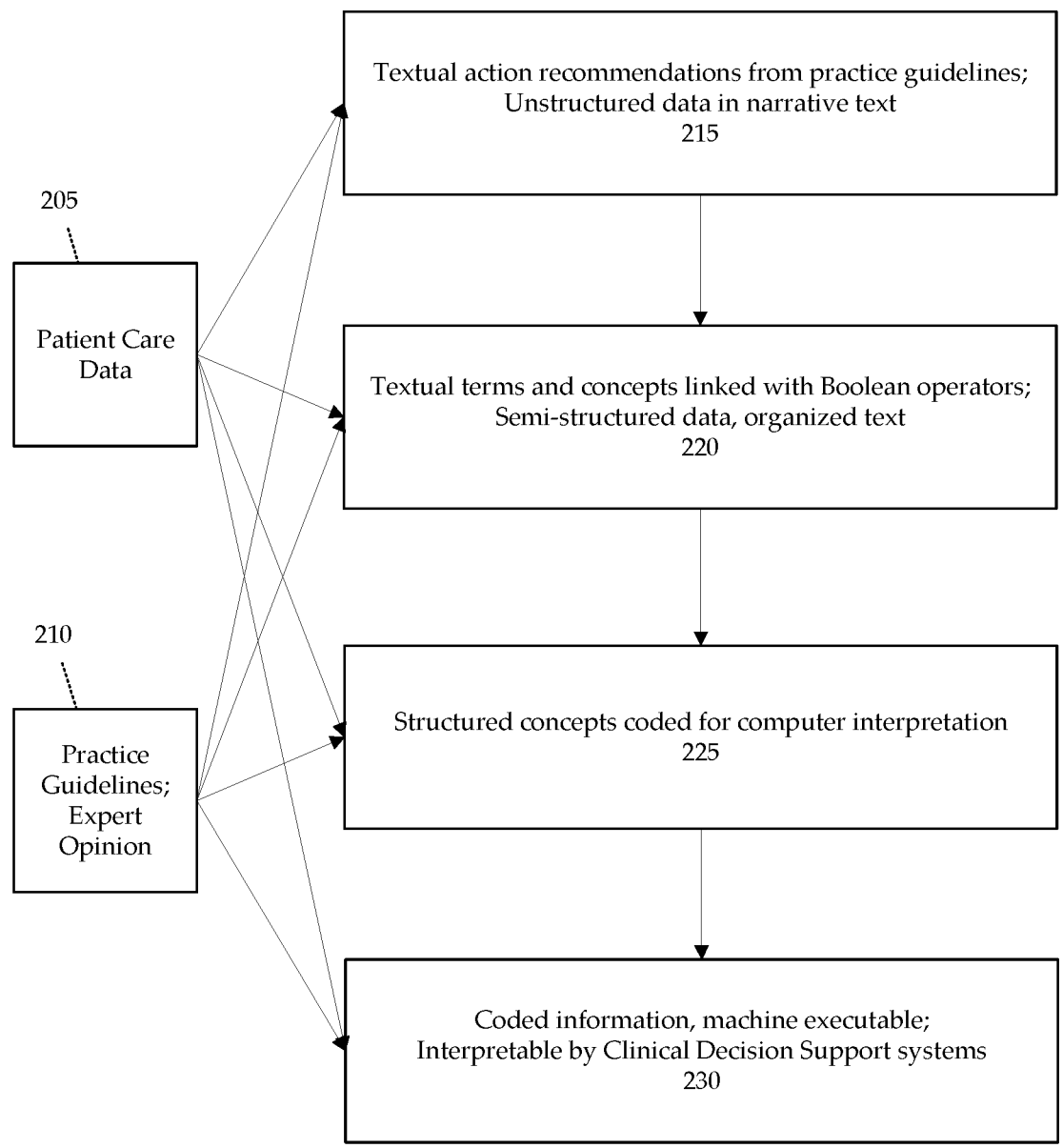
FIG. 2 diagrammatically illustrates an example method of receiving input data in various levels of operable structure.

FIG. 2 diagrammatically illustrates an exemplary implementation of an evidence engine on the secure intelligent networked system. A multilayered knowledge schema may be applied to process the data within the secure intelligent networked system.

The evidence engine may be operated based on measures developed in JavaScript Object Notation (JSON) data interchange format and in the Denominator, Exclusion, Attribution, Numerator (DEAN) structure to facilitate logical query flow. Concepts may be expressed in comprehensive value sets. Minimum denominators may be established using standard techniques, such as Bühlmann-Straub credibility modelling.

In some embodiments, the multilayered knowledge schema may be adapted from Boxwala et al., "A Multi-Layered Framework for Disseminating Knowledge for Computer-Based Decision Support."

In such embodiments, the data received may have any level of structure, including unstructured narrative format 215. The narrative text may include patient care data 205 received from physician-submitted commercial insurance claims, customer claims, or Medicare claims. The narrative text may also include textual recommendations from practice guidelines or expert opinion and may be curated by subject matter expert panels 210.

The received data may be semi-structured 220, with terms and concepts linked to Boolean operators. Logic operations may then produce recommendations regarding the interventions that are possible in a specified clinical scenario.

The received data may be further specified with sufficient structure as to be coded and interpretable by a computer 225. In this structured state, the text formally defines all data elements and logic required to use a computer based Clinical Decision Support system.

The received data may be further structured in machine-executable format for use in various Clinical Decision Support systems 230. Clinical knowledge may then be implemented within a specified setting and workflow.

Range of Better Practice

The Range of Better Practice refers to the limits of appropriate measures, where an Appropriateness Measures score may exceed an upper threshold in the case of overuse of an action, or lower threshold in the case of underuse of an action.

Figure 3:
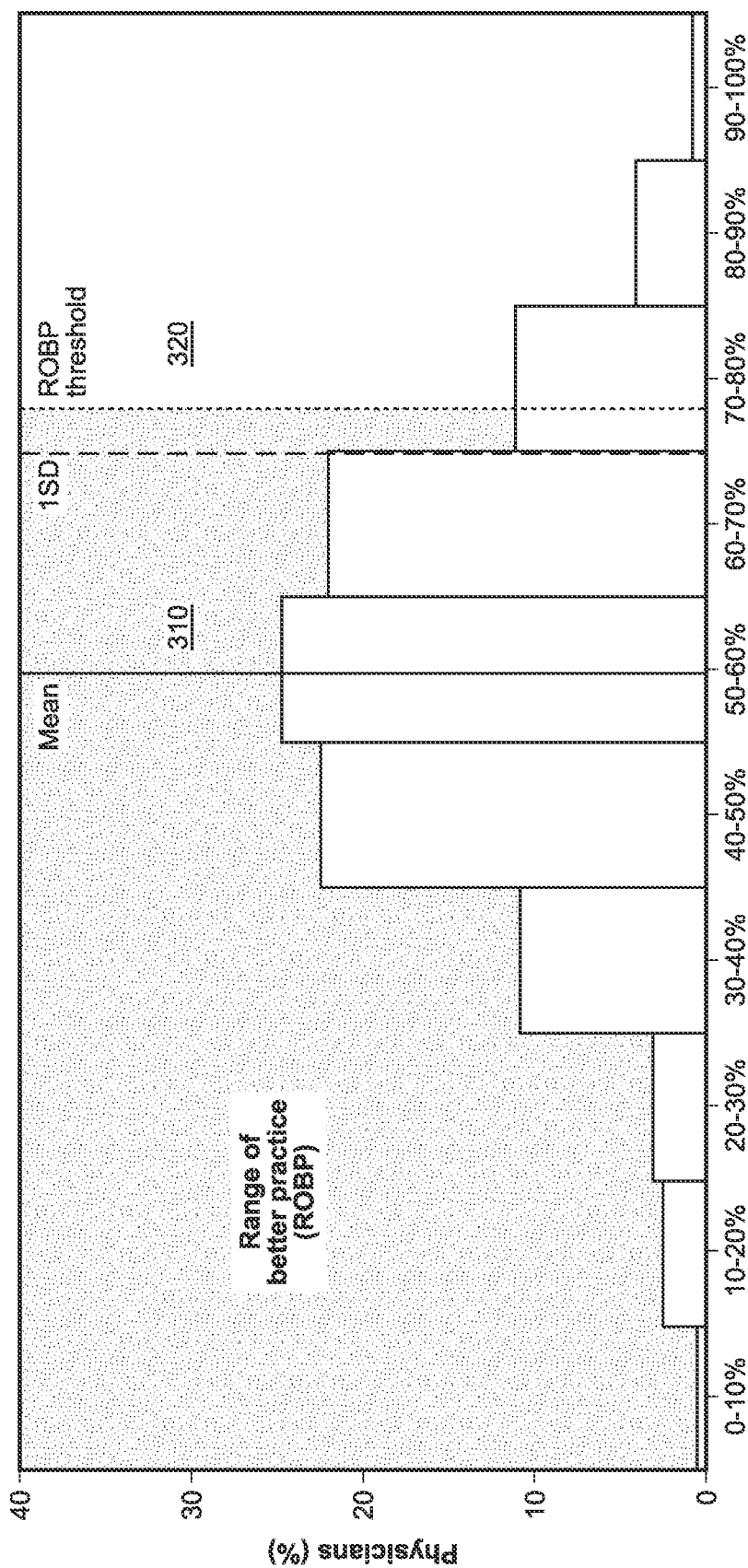
FIG. 3 is an example method of presenting the output or outputs of the system and method described herein.

FIG. 3 illustrates an Appropriateness measure 310 in context with the Range of Better Practice 320. The Range of Better Practice can be determined first by statistical analysis of claims data such as identification of outliers on a Gaussian curve. Algorithms may be implemented within the network to adjust for factors that may not be apparent from the claims data.

Figure 4A:
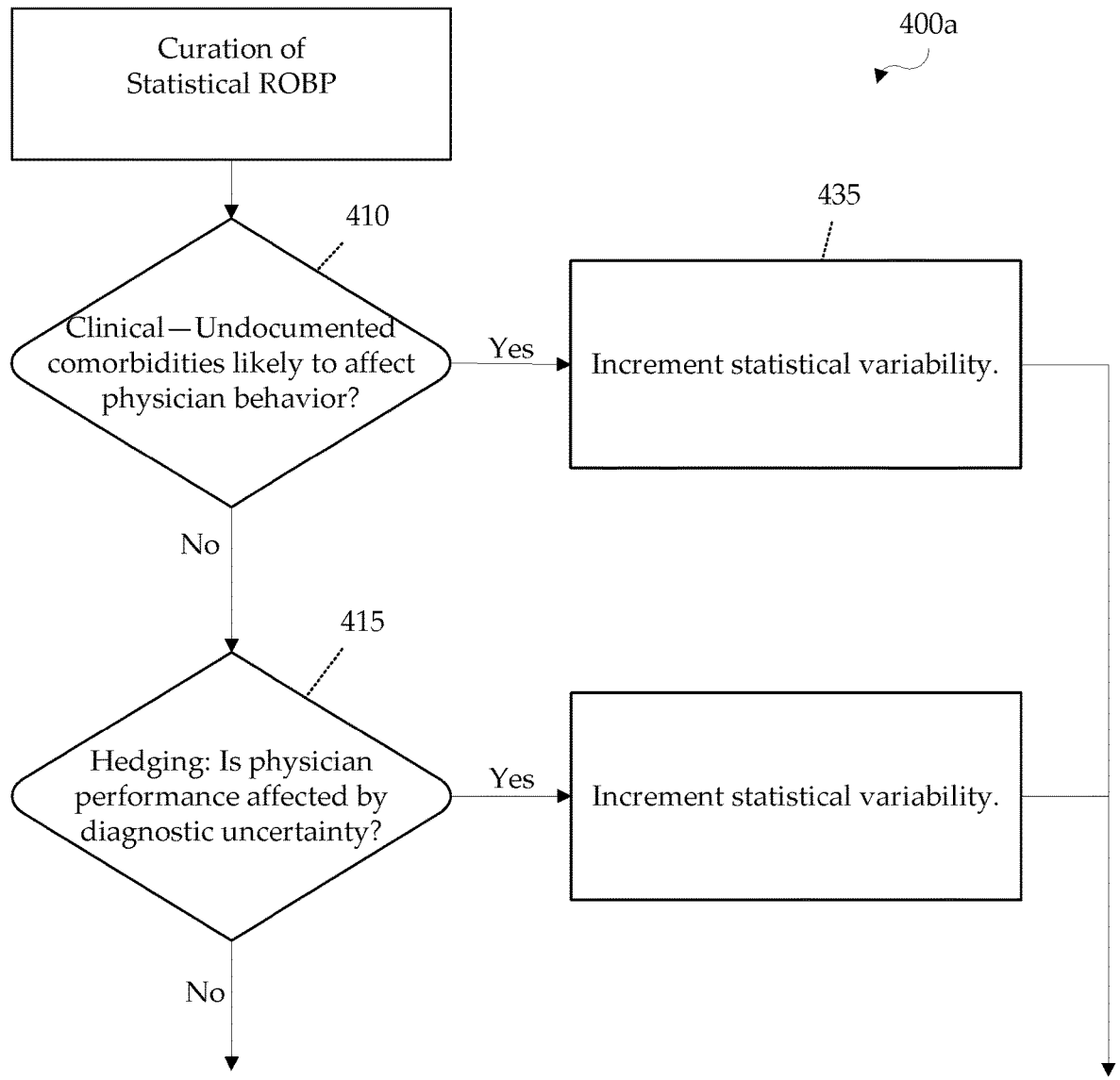
FIGS. 4A-C diagrammatically illustrate a flowchart related to adjustment of weighted values as used in the present disclosure.
Figure 4B:
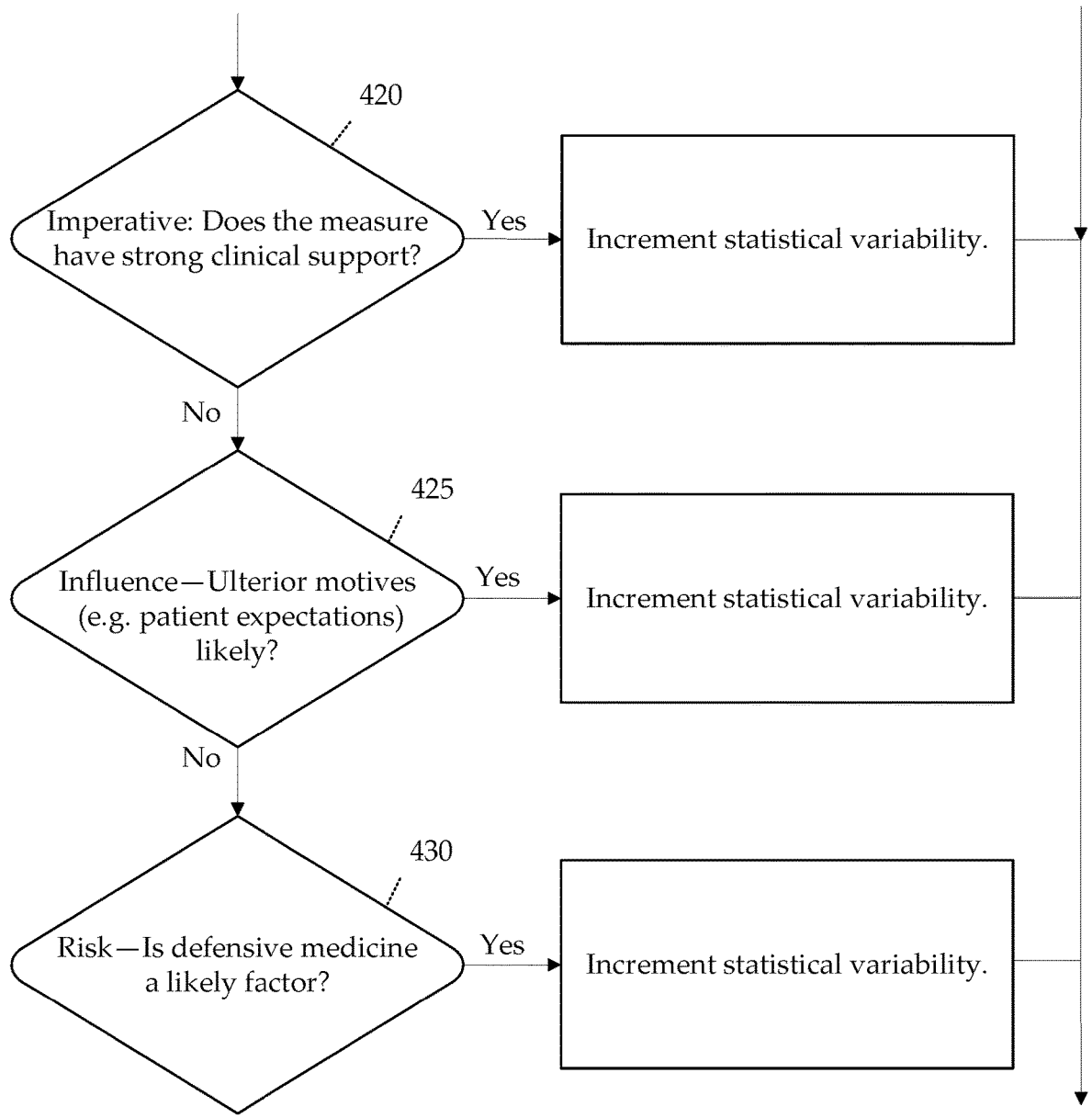
Figure 4C:
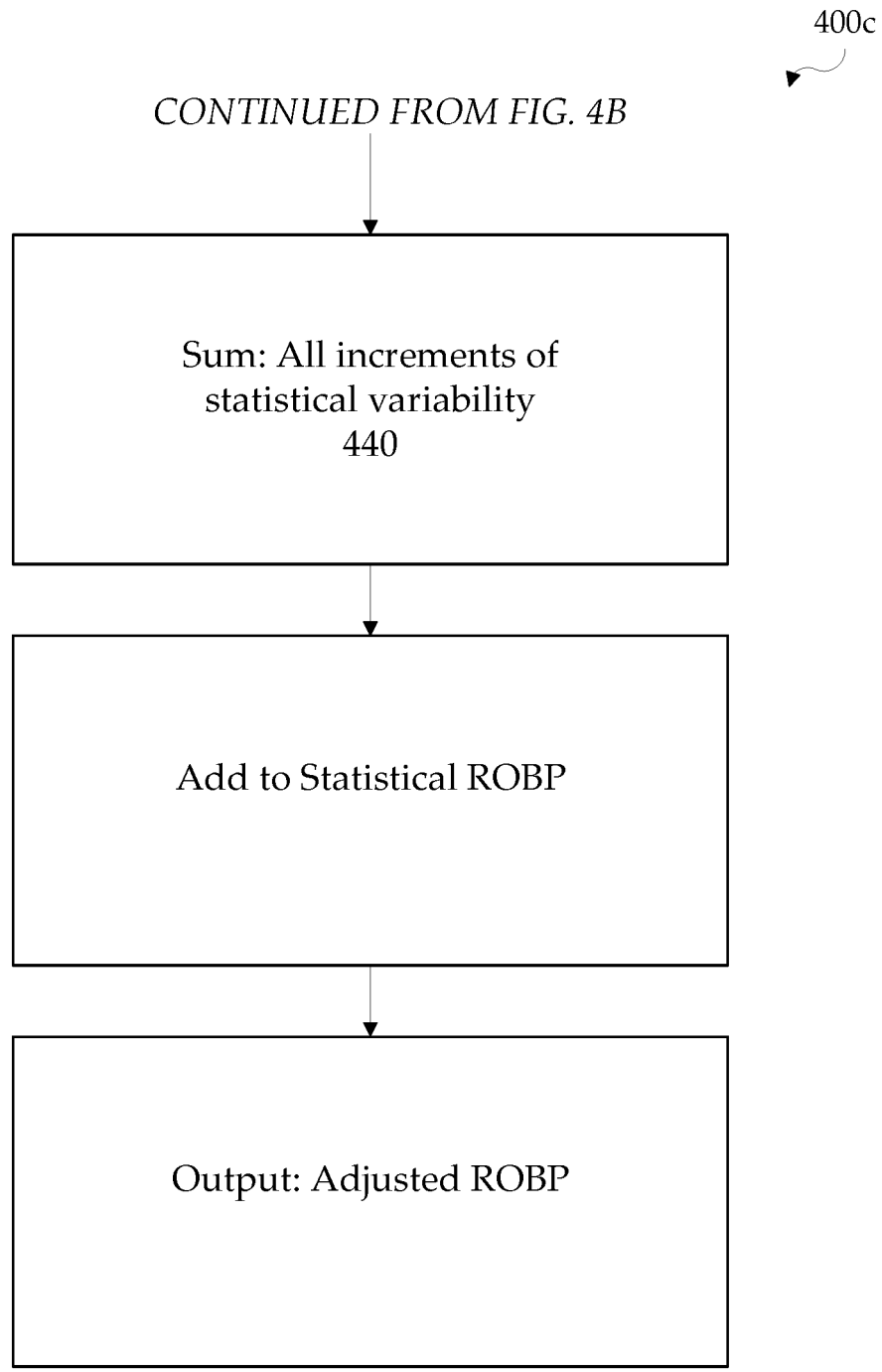

FIG. 4 illustrates an algorithm 400*a*, 400*b*, 400*c* that may be used to adjust for factors that may be lacking in claims data.

In one embodiment of the algorithm, such factors may include undocumented comorbidities 410; hedging in the face of diagnostic uncertainty 415; strength of clinical support 420; ulterior factors such as patient expectations 425; or defensive practice to reduce any risk of malpractice liability 430.

Each such factor may add one increment of variability 435. The sum of such increments can be used to adjust the Range of Better Practices as appropriate 440.

In the example of nuclear stress testing, clear overuse of nuclear stress testing was found where more than 65% of cardiovascular stress testing implemented were unnecessary, or otherwise inappropriate, nuclear stress tests.

Appropriate Practice

The disclosed methods further allow for a cumulative Appropriate Practice Score 140 (in FIG. 1) to reflect a physician's performance across multiple measures or practice areas.

Figure 5:
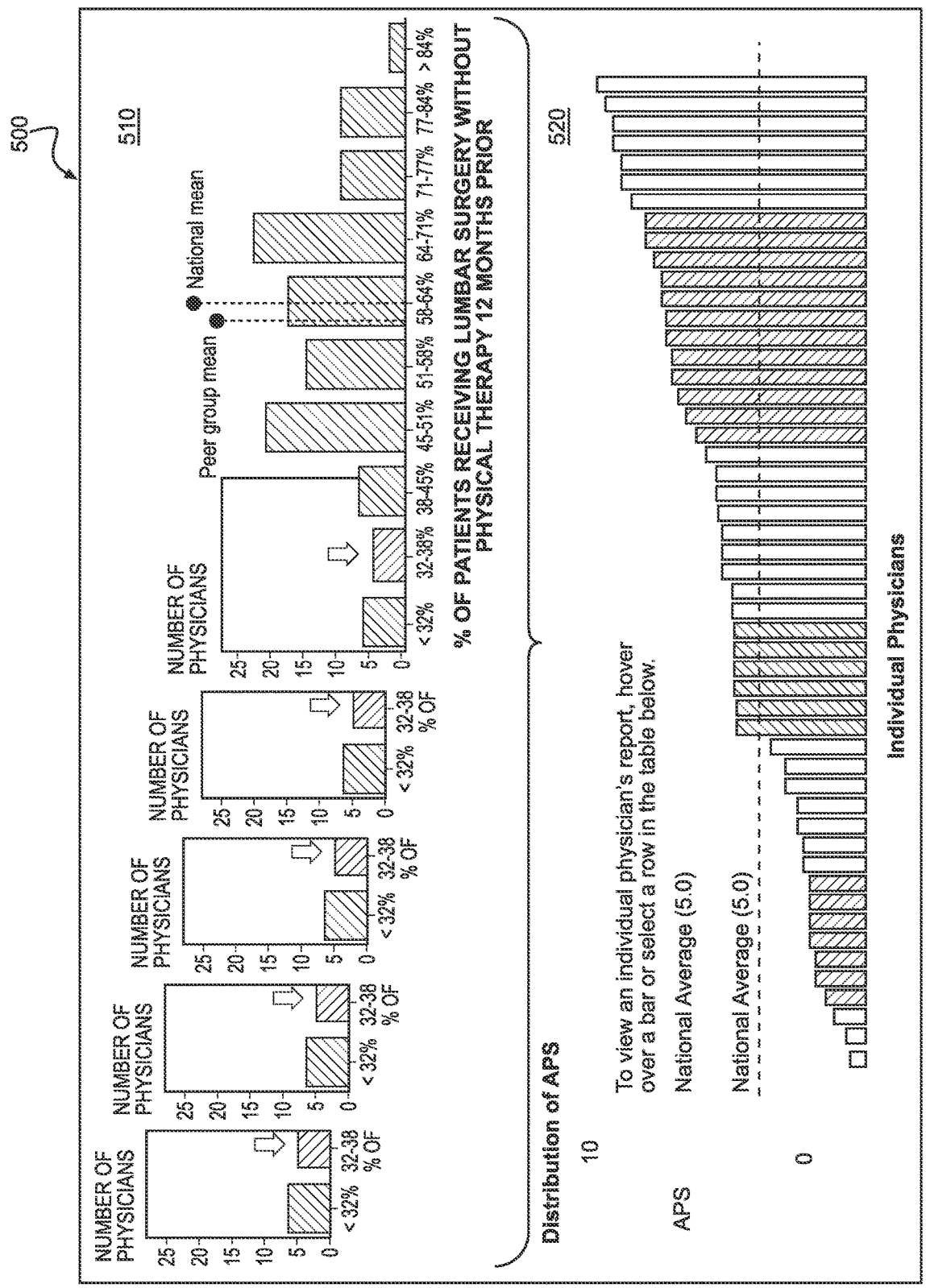
FIG. 5 is a further example method of presenting and contextualizing the output or outputs of the system and method described herein.

FIG. 5 is an exemplary method 500 of determining and displaying the Appropriate Practice Score. Individual Appropriateness Measures scores, in context with the Range of Better Practice, are accumulated 510 and reflected in a distribution of Appropriate Practice Scores for a plurality of physicians 520.

Appropriateness Measures scores may be weighted more heavily in the overall Appropriate Practice Score when the measures are more costly, more harmful, or practiced more frequently by an individual physician.

Figure 6:
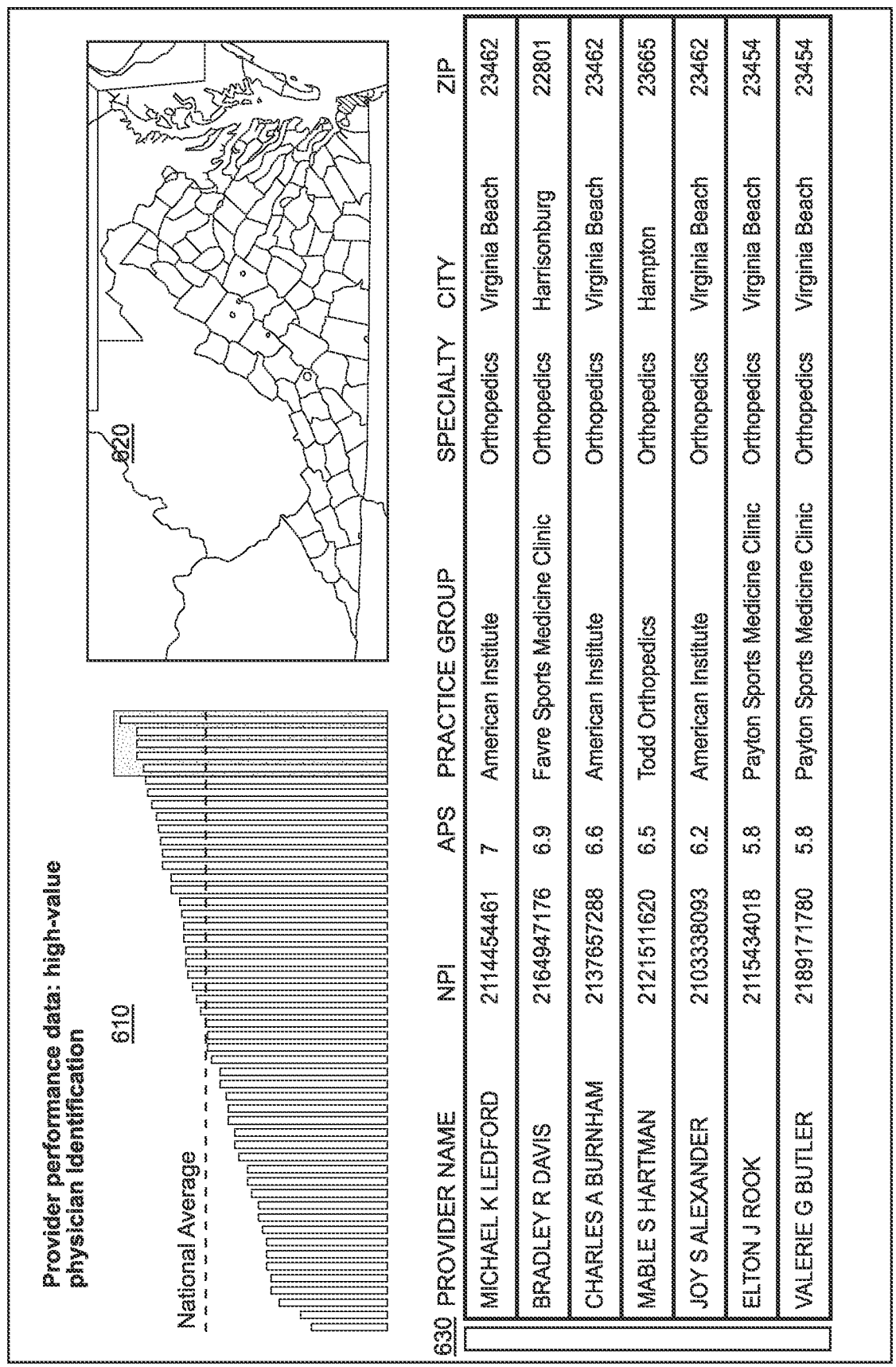
FIG. 6 is a further example method of presenting and contextualizing the output or outputs of the system and method described herein.

FIG. 6 shows an exemplary method of displaying the output for Appropriate Practice Scores. Appropriate Practice Scores may be compared and evaluated with a national average 610, or may be searched by region 620. Physician rankings by region or practice area 630 may also be displayed.

Figure 7:
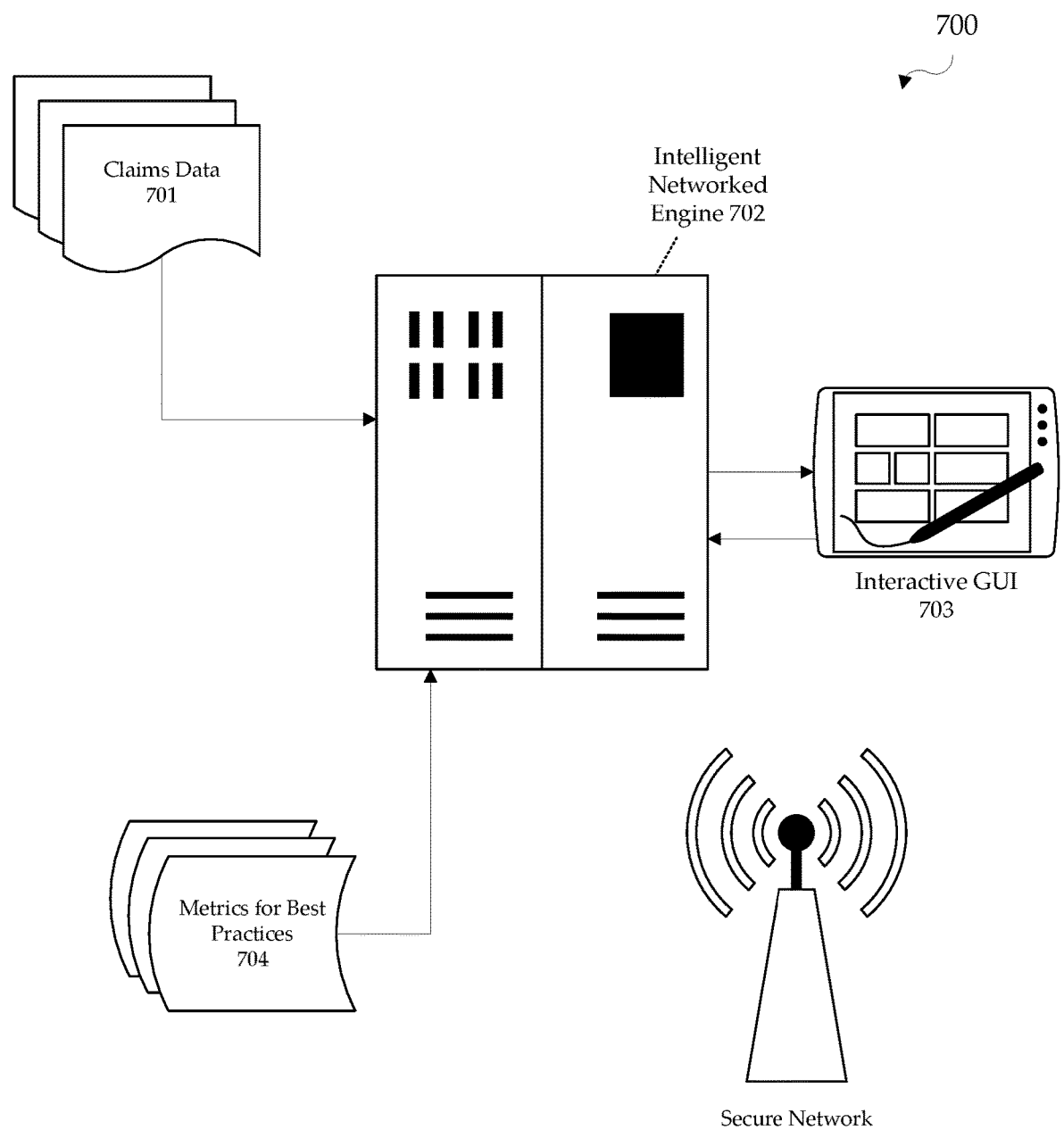
FIG. 7 is an exemplary embodiment of the secure intelligent network on which the disclosure may be implemented.

FIG. 7 shows an exemplary embodiment 700 of the secure intelligent network on which the disclosure may be implemented. Physician-submitted claims data 701 may be received by the intelligent networked engine 702, which may be comprised of a plurality of nodes operating according to a set of metrics 704. The outputs described herein may be displayed on an interactive graphic user interface 703 which may return further data to adjust values stored within the intelligent networked engine, or which may supplement the claims data as initially submitted. Such supplementation may modify or validate any output generated by the intelligent networked engine in accordance with best practice based on unique or specific circumstances.

Figure 8:
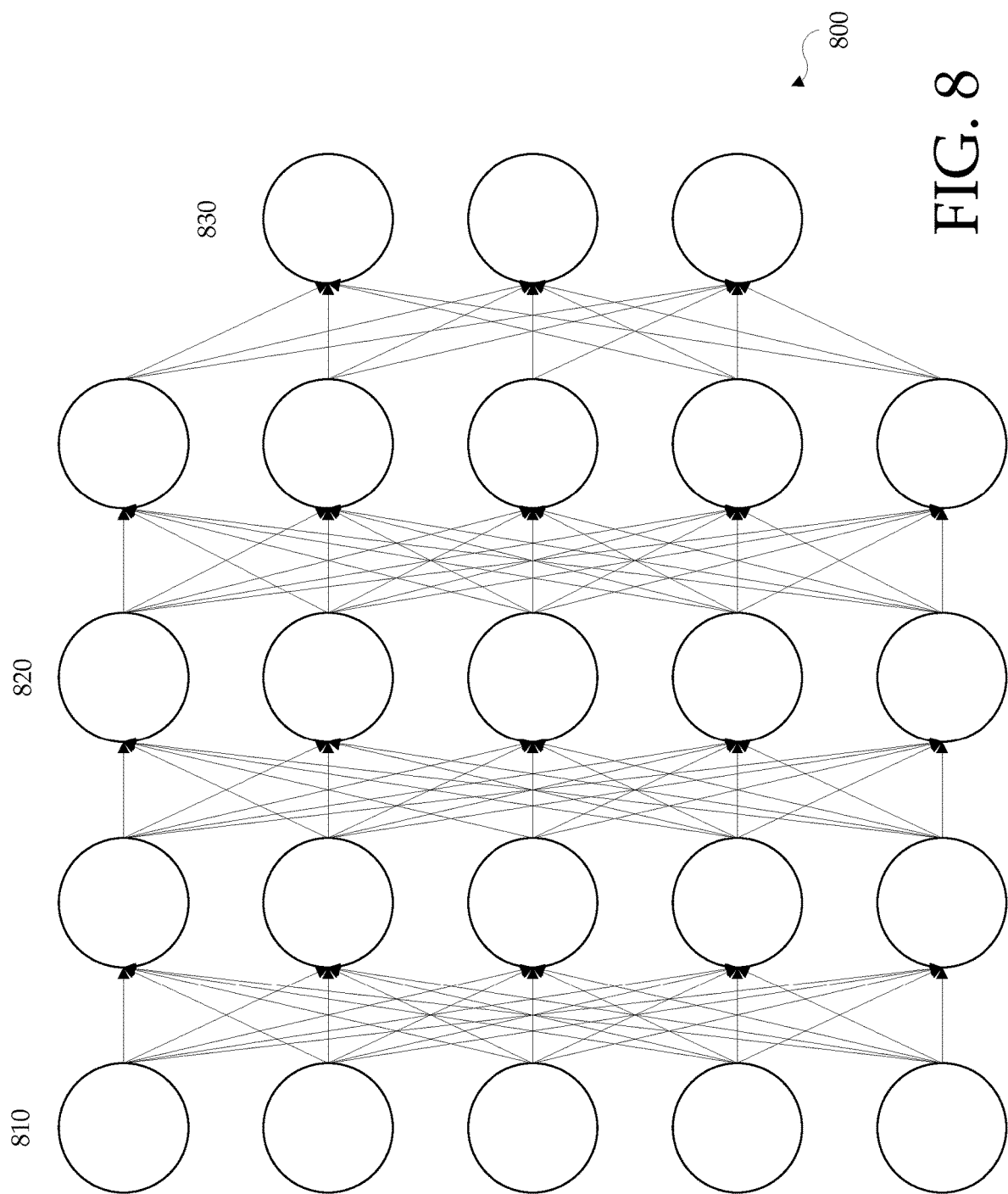
FIG. 8 is an exemplary embodiment of a deep neural network, as may be used in the present disclosure.

FIG. 8 shows an exemplary deep neural network 800 which may be used in the implementation. The exemplary embodiment here comprises an input node 810, a plurality of intermediary nodes 820, and an output node 830, each node having weights, biases, functions, and thresholds that are implemented and tuned for optimally useful results.

What is claimed is:

1. An intelligent secure networked system for identifying and correcting a defect in a health care service, the system comprising:
   a computer processor for processing data;
   a storage medium communicatively coupled to the computer processor, the storage medium storing data;
   a secure intelligent network communicatively coupled to the computer processor and the storage medium, the secure intelligent network having a deep neural network, the deep neural network trained by an evidence engine with evidentiary support including medical journals, health studies, clinical guidelines, or standards bodies, the deep neural network comprising:
   a first input node configured to receive a set of data comprising physician-directed health care service data for a previous stress test as coded and unstructured narrative text, and health care service data as the health care service is being delivered, the first input node configured to adjust for a factor lacking in claims data including undocumented comorbidities, hedging in diagnostic uncertainty, strength of clinical support, ulterior motives, defensive medicine, a presence for each factor equating to incremental statistical variability that is calculated to a sum, added to a statistical range of better practice and results in an adjusted range of better practice;
   a second input node configured to receive a set of metrics associated with appropriateness of a stress test;
   a plurality of intermediary nodes, the plurality of intermediary nodes having a weight, bias and threshold directing an analysis by the deep neural network on the physician-directed health care service data for the stress test;
   a first output node generating a first output comprising a knowledge narrative representing a plain-text description of an appropriateness measure for the stress test and a range of better practice comprising limits of the appropriateness measure, where an appropriateness measures score exceeds an upper limit in a case of overuse of a service, or is below a lower limit in a case of underuse of a service that results from operation of the deep neural network on input elements;
   a second output node generating a second output that comprises a rate of inappropriateness of the stress test, the inappropriateness having a numerator representing a number of stress tests with nuclear imaging that occurred within thirty days of the evaluation and management visit to the cardiologist and having a denominator representing stress testing that occurred within thirty days of the evaluation and management visit to the cardiologist, excluding cases with inpatients, outpatients with symptoms of acute coronary syndrome or patients who had a cardiac-related emergency department visit within a thirty day period;
   a dynamic feedback communicatively coupling the knowledge narrative and range of better practice node and the rate of inappropriateness of the stress test for the health care service for continuous learning of the deep neural network;
   a third output node comprising the appropriateness measures score for cardiovascular stress testing; and
   a fourth output node comprising a cumulative appropriateness practice score to reflect a physician's performance across multiple measures or practice areas.

2. The system of claim 1, further comprising the physician-directed health care service data that includes data received from a physician-submitted insurance claim.

3. The system of claim 1, further comprising the physician-directed health care service data that includes a diagnosis or a treatment plan.

4. The system of claim 1, further comprising a set of metrics including data regarding a medical standard of care.

5. The system of claim 4, further comprising the set of metrics including data regarding a cost of a medical service.

6. The system of claim 4, further comprising the set of metrics including data received from a commercial claim.

7. The system of claim 4, further comprising the set of metrics including data received from a customer claim.

8. The system of claim 4, further comprising the set of metrics including data received from a Medicare claim.

9. The system of claim 1, further comprising the second output node generating an output that comprises a plain text recommended action for a specific patient.

10. The system of claim 1, further comprising the evidence engine configured with:
    textual action recommendations from practice guidelines;
    unstructured data in narrative text;
    textual terms and concepts linked with Boolean operators;
    semi-structured data;
    organized text;
    structured concepts coded for computer interpretation; and
    coded information, machine executable, interpretable by clinical decision support systems.

11. A method for identifying and correcting a defect in a health care service, comprising:
    training a deep neural network by an evidence engine, the deep neural network trained with evidentiary support including medical journals, health studies, clinical guidelines, or standards bodies, the deep neural network;

receiving, by a first input node of a secure intelligent networked engine having the deep neural network, a set of data comprising physician-directed health care service data for a previous stress test as coded and unstructured narrative text, and health care service data as the health care service is being delivered, the first input node configured to adjust for a factor lacking in claims data including undocumented comorbidities, hedging in diagnostic uncertainty, strength of clinical support, ulterior motives, defensive medicine, a presence for each factor equating to incremental statistical variability that is calculated to a sum, added to a statistical range of better practice and results in an adjusted range of better practice;

receiving, by a second input node of the secure intelligent networked engine having the deep neural network, a set of metrics associated with appropriateness of a stress test;

configuring a plurality of intermediary deep neural network nodes having a weight, bias and threshold directing an analysis by the deep neural network on the physician-directed health care service data for the stress test;

generating a first output node comprising a knowledge narrative representing a plain text description of an appropriateness measure for the stress test and a range of better practice comprising limits of the appropriateness measure, where an appropriateness measures score exceeds an upper limit in a case of overuse of a service, or is below a lower limit in a case of underuse of a service that results from operation of the deep neural network on the input elements;

generating a second output node comprising a rate of inappropriateness of the stress test, the inappropriateness having a numerator representing a number of stress tests with nuclear imaging that occurred within thirty days of an evaluation and management visit to a cardiologist and having a denominator representing stress testing that occurred within thirty days of the evaluation and management visit to the cardiologist, excluding cases with inpatients, outpatients with symptoms of acute coronary syndrome or patients who had a cardiac-related emergency department visit within a thirty day period;

generating a dynamic feedback communicatively coupling the knowledge narrative and range of better practice node and the rate of inappropriateness of the stress test for a specific health care service for continuous learning of the deep neural network;

generating a third output node comprising the appropriateness measures score for cardiovascular stress testing; and generating a fourth output node comprising a cumulative appropriateness practice score to reflect a physician's performance across multiple measures or practice areas.

12. The method of claim 11, further comprising the physician-directed health care service data including data received from a physician-submitted insurance claim.

13. The method of claim 11, further comprising the physician-directed health care service data including a diagnosis or treatment plan.

14. The method of claim 11, further comprising input for a set of metrics that is received from published guidelines, medical journals, standards organizations, or expert opinion.

15. The method of claim 14, further comprising the set of metrics including data regarding a medical standard of care.

16. The method of claim 14, further comprising the set of metrics including data regarding a cost of a medical service.

17. The method of claim 14, further comprising the set of metrics including data received from a commercial claim.

18. The method of claim 14, further comprising the set of metrics including data received from a customer claim.

19. The method of claim 14, further comprising the set of metrics including data received from a Medicare claim.

20. The method of claim 11, further comprising the second output node generating an output including a plain text recommended action for a specific patient.

21. A non-transitory computer-readable storage medium having embodied thereon instructions, which when executed by a processor, perform steps of a method, the method comprising:

training a deep neural network, the deep neural network trained by an evidence engine with evidentiary support including medical journals, health studies, clinical guidelines, or standards bodies, the deep neural network;

receiving, by a first input node, physician-directed health care service data for a previous stress test as coded and unstructured narrative text, the first input node configured to adjust for a factor lacking in claims data including undocumented comorbidities, hedging in diagnostic uncertainty, strength of clinical support, ulterior motives, defensive medicine, a presence for each factor equating to incremental statistical variability that is calculated to a sum, added to a statistical range of better practice and results in an adjusted range of better practice;

receiving, by a second input node, a set of metrics associated with appropriateness of a stress test;

configuring a plurality of intermediary deep neural network nodes, the plurality of intermediary deep neural network nodes having a weight, bias and threshold directing an analysis of the deep neural network on physician-directed health care service data for the stress test;

generating, by a secure intelligent networked engine having the deep neural network, a first output node comprising a knowledge narrative representing a plain-text description of an appropriateness measure for the stress test and a range of better practice comprising limits of the appropriateness measure, where an appropriateness measures score exceeds an upper limit in a case of overuse of a service, or is below a lower limit in a case of underuse of a service that results from operation of the deep neural network on input elements;

generating, by the secure intelligent networked engine having the deep neural network, a second output node generating a second output that comprises a rate of inappropriateness of the stress test, the inappropriateness having a numerator representing a number of stress tests with nuclear imaging that occurred within thirty days of an evaluation and management visit to a cardiologist and having a denominator representing stress testing that occurred within thirty days of the evaluation and management visit to the cardiologist, excluding cases with inpatients, outpatients with symptoms of acute coronary syndrome or patients who had a cardiac-related emergency department visit within a thirty day period;

generating a dynamic feedback communicatively coupling the knowledge narrative and range of better practice node and the rate of inappropriateness of the stress test for a specific health care service for continuous learning of the deep neural network;

generating a third output node comprising the appropriateness measures score for cardiovascular stress testing; and generating a fourth output node comprising a cumulative appropriateness practice score to reflect a physician's performance across multiple measures or practice areas.

* * * * *